(12) United States Patent
Bang et al.

(10) Patent No.: US 10,208,130 B2
(45) Date of Patent: Feb. 19, 2019

(54) QUANTIFYING HER2 PROTEIN FOR OPTIMAL CANCER THERAPY

(71) Applicant: Expression Pathology, Inc., Rockville, MD (US)

(72) Inventors: Yung-Jue Bang, Seoul (KR); Todd Hembrough, Gaithersburg, MD (US); Eunkyung An, Bethesda, MD (US); Do-Youn Oh, Seoul (KR)

(73) Assignees: Expression Pathology, Inc., Rockville, MD (US); Department of Internal Medicine and Cancer Research, Seoul National University Hospital, Seoul (KR)

( * ) Notice: Subject to any disclaimer, the term of this patent is extended or adjusted under 35 U.S.C. 154(b) by 0 days.

(21) Appl. No.: 15/169,724

(22) Filed: May 31, 2016

(65) Prior Publication Data

US 2016/0349259 A1 Dec. 1, 2016

Related U.S. Application Data

(60) Provisional application No. 62/168,709, filed on May 29, 2015, provisional application No. 62/310,639, filed on Mar. 18, 2016.

(51) Int. Cl.
*C07K 16/32* (2006.01)
*A61K 39/395* (2006.01)
*A61K 39/00* (2006.01)

(52) U.S. Cl.
CPC ........ *C07K 16/32* (2013.01); *A61K 39/39558* (2013.01); *A61K 2039/505* (2013.01); *G01N 2333/71* (2013.01); *G01N 2333/91205* (2013.01); *G01N 2560/00* (2013.01)

(58) Field of Classification Search
None
See application file for complete search history.

(56) References Cited

U.S. PATENT DOCUMENTS

| 7,473,532 B2 | 1/2009 | Darfler et al. |
| 2013/0071384 A1 | 3/2013 | Andya et al. |
| 2013/0095172 A1 | 4/2013 | Alavattam et al. |
| 2013/0302328 A1 | 11/2013 | Krizman et al. |

FOREIGN PATENT DOCUMENTS

| WO | 2008/097229 A1 | 8/2008 | |
| WO | WO 2012/170715 | * 11/2013 | ............. C40B 30/04 |

OTHER PUBLICATIONS

Catenacci et al. (PLOS One, 9(7): 1-14, Jul. 2014).*
International Search Report, Application No. PCT/US16/35118, dated Sep. 16, 2016, 4 pages.
Lange, V., et al.: "Selected reaction monitoring for quantitative proteomics: a tutorial", *Molecular Systems Biology*, 2008, vol. 4, No. 222, pp. 1-14.
Sano, S., et al.: "Absolute Quantitation of Low Abundance Plasma APL1B peptides at Sub-fmol/mL Level by SRM/MRM without Immunoaffinity Enrichment", *Journal of Proteome Research*, 2014, vol. 13, pp. 1012-1020.
Yardley et al., "Quantitative measurement of HER2 expression in breast cancers: comparison with 'real-world' routine HER2 testing in a multicenter Collaborative Biomarker Study and correlation with overall survival" Breast Cancer Research 17:41(2015).

* cited by examiner

*Primary Examiner* — Nelson B Moseley, II
(74) *Attorney, Agent, or Firm* — Edell, Shapiro & Finnan, LLC.

(57) ABSTRACT

Improved methods of treatment are provided for patients suffering from cancer. The methods identify whether a tumor will be responsive to treatment with a therapeutic regime that includes anti-Her2 therapeutic agents. A specific Her2 fragment peptide is precisely quantitated by SRM-mass spectrometry directly in tumor cells collected from tumor tissue that was obtained from a cancer patient and compared to a reference level in order to determine if the cancer patient will positively respond to treatment with a therapeutic agent that specifically targets the Her2 protein.

16 Claims, 2 Drawing Sheets

Specification includes a Sequence Listing.

Cohort 1: HER2-positive treated with trastuzumab and chemotherapy;
Cohort 2: HER2-positive treated with chemotherapy alone Cohort 1: HER2-positive treated with trastuzumab and chemotherapy;
Cohort 2: HER2-positive treated with chemotherapy alone

SEQUENCE LISTING

```
<160> NUMBER OF SEQ ID NOS: 1

<210> SEQ ID NO 1
<211> LENGTH: 8
<212> TYPE: PRT
<213> ORGANISM: Homo sapiens

<400> SEQUENCE: 1

Glu Leu Val Ser Glu Phe Ser Arg
1               5
```

QUANTIFYING HER2 PROTEIN FOR OPTIMAL CANCER THERAPY

This application claims the benefit of U.S. Provisional Application No. 62/168,709 filed May 29, 2015 and U.S. Provisional Application No. 62/310,639 filed Mar. 18, 2016, each entitled "Quantifying Her2 Protein for Optimal Cancer Therapy." This application also contains a sequence listing submitted electronically via EFS-web, which serves as both the paper copy and the computer readable form (CRF) and consists of a file entitled "001152_8047_US02_SEQ_LISTING", which was created on May 31, 2016, which is 444 bytes in size, and which is also incorporated by reference in its entirety.

INTRODUCTION

Methods are provided for treating cancer patients by assaying tumor tissue from patients and identifying those patients most likely to respond to treatment with anti-Her2 therapeutic agents. The level of Her2 expression in the tumor tissue is determined by quantitating a specified peptide derived from subsequences of the full-length Her2 protein (also referred to as the Neu proto-oncogene, c-ErbB-2, tyrosine kinase-type cell surface receptor HER2, p185erbB2, and CD340), and this level is compared to a reference level. If the level of Her2 expression is higher than the reference level the patient is treated with a regimen that includes at least one anti-Her2 therapeutic agent, whereas if the level is below the reference level the patient is treated with a regimen that does not include an anti-Her2 agent.

The specified peptide is detected using mass spectrometry-based Selected Reaction Monitoring (SRM), also referred to as Multiple Reaction Monitoring (MRM), and which is referred to herein as an SRM/MRM assay. An SRM/MRM assay is used to detect the presence and quantitatively measure the amount of the specified Her2 fragment peptide, directly in cells procured from cancer patient tissue, such as, for example formalin fixed cancer tissue. The amount of the peptide allows quantitation of the amount of intact Her2 protein in the tumor sample. Specific and optimized therapeutic agents and treatment strategies can be used to treat an individual cancer patient's disease based on how much of the Her2 protein is present in their cancer cells.

SUMMARY OF THE INVENTION

Methods are provided for treating a patient suffering from cancer. The steps if the methods include:

(a) quantifying the level of a specified Her2 fragment peptide in a protein digest prepared from a tumor sample obtained from the patient and calculating the level of the Her2 peptide in said sample by selected reaction monitoring using mass spectrometry;

(b) comparing the level of said Her2 fragment peptide to a reference level, and (c) treating the patient with a therapeutic regimen containing an effective amount of an anti-Her2 therapeutic agent when the level of the Her2 fragment peptide is higher than the reference level or (d) treating the patient with a therapeutic regimen that does not comprise an effective amount of an anti-Her2 therapeutic agent when the level of the Her2 fragment peptide is below the reference level.

The reference level may be about 1825 amol/µg, +/−250 amol/µg, +/−150 amol/µg, +/−100 amol/µg, +/−50 amol/µg, +/−25 amol/µg, of biological sample protein analyzed and the cancer may be, for example, gynecological, esophageal, gallbladder, pancreatic, breast or lung cancer. Advantageously the cancer is gastric cancer.

The protein digest of the biological sample may be prepared by the Liquid Tissue protocol. The protein digest may comprise a protease digest, such as, for example, a trypsin digest.

The method of mass spectrometry may include tandem mass spectrometry, ion trap mass spectrometry, triple quadrupole mass spectrometry, MALDI-TOF mass spectrometry, MALDI mass spectrometry, hybrid ion trap/quadrupole mass spectrometry and/or time of flight mass spectrometry. The mode of mass spectrometry used may be, for example, Selected Reaction Monitoring (SRM), Multiple Reaction Monitoring (MRM), and/or multiple Selected Reaction Monitoring (mSRM). In these methods the specified Her2 peptide may have the amino acid sequence as set forth as SEQ ID NO:1.

The tumor sample may be a cell, collection of cells, or a solid tissue, and may be formalin fixed solid tissue, including paraffin embedded tissue. The specified Her2 fragment peptide may advantageously be quantified by comparison to a spiked internal standard peptide of known amount, where both the native peptide in the biological sample and the internal standard peptide correspond to the same amino acid sequence of the Her2 fragment peptide as shown in SEQ ID NO:1. Advantageously the internal standard peptide is an isotopically labeled peptide, labeled with, for example, one or more heavy stable isotopes selected from $^{18}O$, $^{17}O$, $^{15}N$, $^{13}C$, $^{2}H$ or combinations thereof.

The measurement of the specified Her2 fragment peptide may be combined with detecting and quantitating other peptides from other proteins in a multiplex format so that the treatment decision about which agent used for treatment is based upon specific levels of the specified Her2 fragment peptide in combination with other peptides/proteins in the biological sample.

In the methods described above, when the level of the specified peptide is higher than the reference level, then the anti-Her2 therapeutic agent may include trastuzumab, whereas when the level of the specified peptide is lower than the reference level, then therapeutic treatment does not include trastuzumab.

DETAILED DESCRIPTION

Figure 1:
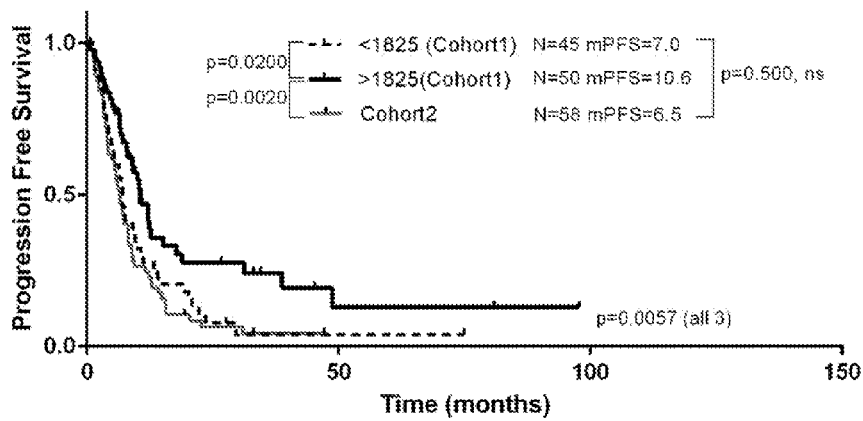
FIG. 1 shows a comparison of progression-free survival of patients treated with trastuzumab plus chemotherapy versus treatment with chemotherapy alone. The data compare patients with Her2>1825 amol/µg and those with Her2<1825 amol/µg.

Quantitative methods are provided for determining if a cancer patient will clinically respond in a favorable manner to cancer therapeutic agents that specifically target the Her2 protein. Specifically, diagnostic methods for measuring Her2 protein in a tumor sample or samples from the patient are provided and the resulting quantitative data are used to guide subsequent treatment decisions for that patient. The sample is advantageously formalin-fixed. Using an SRM/

MRM assay that measures a specific Her2 peptide fragment, and particular characteristics about this peptide, the amount of Her2 in cells derived from formalin fixed paraffin embedded (FFPE) tissue is determined. The peptide fragment derives from the intracellular domain of the full-length Her2 protein (ICD) and has the sequence ELVSEFSR. Surprisingly it has been found that this peptide can be reliably detected and quantitated in digests prepared from FFPE samples of tumor tissue. See U.S. patent application Ser. No. 13/993,045, the contents of which are hereby incorporated by reference in their entirety.

More specifically, this SRM/MRM assay can measure this peptide directly in complex protein lysate samples prepared from cells procured from patient tissue samples, such as formalin fixed cancer patient tissue. Methods of preparing protein samples from formalin-fixed tissue are described in U.S. Pat. No. 7,473,532, the contents of which are hereby incorporated by reference in their entirety. The methods described in U.S. Pat. No. 7,473,532 may conveniently be carried out using Liquid Tissue reagents and protocol available from Expression Pathology Inc. (Rockville, Md.).

The most widely and advantageously available form of tissue, and cancer tissue, from cancer patients is formalin fixed, paraffin embedded tissue. Formaldehyde/formalin fixation of surgically removed tissue is by far the most common method of preserving cancer tissue samples worldwide and is the accepted convention in standard pathology practice. Aqueous solutions of formaldehyde are referred to as formalin. "100%" formalin consists of a saturated solution of formaldehyde (about 40% by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of the Her2 protein within the specific cancer of the patient from whom the tissue was collected and preserved. This not only provides diagnostic information about the cancer, but also provides objective criteria that guide a physician or other medical professional to appropriate therapy for the patient. In this case, utilizing this assay provides information about specific levels of Her2 protein expression in cancer tissue and indicates whether or not the patient from whom the cancer tissue was obtained will respond in a favorable way to therapy with anti-cancer therapeutic agents designed to specifically inhibit the function and/or reduce the presence of the Her2 protein.

Treating cancer patients with anti-Her2 therapeutic agents is one of the most common and effective strategies for preventing cancer from growing and prolonging the lives of cancer patients, including cancer patients suffering from gynecological, esophageal, gallbladder, pancreatic, breast, lung, and gastric cancers. Gynecological cancers can include, for example, cervical, ovarian, uterine, vaginal, and vulvar cancers.

The Her2 protein is a signal receptor protein expressed on epithelial cells and, normally, Her2 receptors help control how a healthy cell grows, divides, and repairs itself. However, in some cancers the cancer cells make too many Her2 receptors (Her2 protein overexpression). This makes cells grow and divide in an uncontrolled way. In many cases this protein overexpression is accompanied by a Her2 gene that has been amplified, resulting in multiple copies of the gene (known as Her2 gene amplification). In many cases these extra copies of the Her2 gene cause increased expression of Her2 receptors (Her2 protein overexpression). It therefore is useful for a clinician to know if there is too much Her2 protein in a patient's cancer cells because several anti-Her2 therapeutic agents are available to treat cancers that are considered Her2 positive.

Presently there are two basic tests for determining if a cancer patient is a candidate for anti-Her2 treatment strategies. Both tests use thin sections of tumor samples from a patient. The first test is an IHC (immunohistochemistry) test that utilizes an antibody to detect the Her2 protein in cancer cells and seeks to determine if there is too much Her2 protein in those cells. The results of the IHC test can be: 0 (negative), 1+ (also negative), 2+ (borderline), or 3+ (positive-Her2 protein overexpression). The second test is a FISH (Fluorescence In Situ Hybridization) test that seeks to measure if there are too many copies of the Her2 gene in the cancer cells. The results of the FISH test can be positive (Her2 gene amplification) or negative (no Her2 gene amplification). This test infers that Her2 gene amplification results in overexpression of Her2 protein but does not directly provide a measure of Her2 protein expression.

Generally, only cancers that test IHC 3+ or that are FISH positive may respond to the therapeutic agents that target Her2-positive cancers. An IHC 2+ test result is deemed borderline and, if a tumor is scored as IHC 2+, then the tissue is retested with the more precise Her2 FISH test. Neither the IHC nor FISH tests provide quantitative data that are predictive of sensitivity to an anti-HER2 therapeutic agent, such as sensitivity to trastuzumab in a Her2-positive population.

Research has shown that some Her2 status test results may be wrong. This is likely because different labs use different rules for classifying positive and negative Her2 status. Each pathologist running the tests also may use different criteria to decide whether the results are positive or negative. In most cases, this happens when the test results are borderline, meaning that the results are neither strongly Her2-positive nor Her2-negative. In other cases, tissue from one area of a tumor can test Her2-positive while tissue from a different area of the tumor tests Her2-negative. Inaccurate Her2 test results mean that patients diagnosed with cancer may not receive the best possible care. If all or part of a cancer is Her2-positive but test results classify it as HER2-negative, physicians are unlikely to recommend anti-Her2 therapeutic treatment, even though the patient could potentially benefit from those agents. If a cancer is Her2-negative but test results classify it as HER2-positive, physicians may recommend anti-Her2 therapeutic treatment, even though the patient is unlikely to benefit from the treatment and will be exposed to the agent's secondary risks.

Cancers with Her2 gene amplification and/or Her2 protein overexpression are called Her2-positive in pathology reports. Her2-positive cancers tend to grow faster and are more likely to spread and recur compared to Her2-negative cancers. However, therapeutic agents are available that specifically bind to and inhibit Her2 protein function and are prescribed when a patient's tumor tests positive for Her2. For example, the most commonly used anti-Her2 agent is Herceptin (chemical name: trastuzumab), a monoclonal antibody which works by attaching itself to the Her2 receptors on cancer cells and blocking them from receiving growth signals. By blocking these signals, Herceptin may help to slow or even stop the growth of the cancer. In addition to blocking Her2 receptors, Herceptin can also help fight cancer by alerting the immune system to destroy cancer cells to which it binds.

Another anti-Her2 therapeutic option for some patients with advanced Her2-positive cancer is Tykerb (chemical name: lapatinib). Tykerb works by interfering with certain proteins that cause the cell to grow and divide abnormally. Tykerb can be used in combination with other non-Her2 targeted agents such as; 1) Xeloda (chemical name: capecitabine), a type of chemotherapy, used to treat advanced, HER2-positive cancer that has stopped responding to other forms of chemotherapy such as anthracyclines and taxanes, and to Herceptin, 2) Femara (chemical name: letrozole), a type of hormonal therapy, to treat postmenopausal women diagnosed with hormone-receptor-positive, HER2-positive advanced-stage cancer. Other anti-Her2 therapeutic agents include, but are not limited to, pertuzumab (an antibody that inhibits dimerization of Her2 with other HER proteins) and neratinib (a kinase inhibitor that inhibits the kinase activity of Her2 and EGFR).

Thus there is great clinical value in the ability to correctly evaluate quantitative levels of the Her2 protein in tumors, especially tumors, so that the patient will have the greatest chance of receiving the optimum therapy.

Detection of peptides and determining quantitative levels of a specified Her2 fragment peptide are determined in a mass spectrometer by the SRM/MRM methodology, whereby the SRM/MRM signature chromatographic peak area of each peptide is determined within a complex peptide mixture present in a Liquid Tissue lysate (see U.S. Pat. No. 7,473,532, as described above). Quantitative levels of the Her2 protein are then determined by the SRM/MRM methodology whereby the SRM/MRM signature chromatographic peak area of an individual specified peptide from the Her2 protein in one biological sample is compared to the SRM/MRM signature chromatographic peak area of a known amount of a "spiked" internal standard for the individual specified Her2 fragment peptide.

In one embodiment, the internal standard is a synthetic version of the same exact Her2 fragment peptide that contains one or more amino acid residues labeled with one or more heavy isotopes. Such isotope labeled internal standards are synthesized so that mass spectrometry analysis generates a predictable and consistent SRM/MRM signature chromatographic peak that is different and distinct from the native Her2 fragment peptide chromatographic signature peak and which can be used as a comparator peak. Thus when the internal standard is spiked in known amounts into a protein or peptide preparation from a biological sample and analyzed by mass spectrometry, the SRM/MRM signature chromatographic peak area of the native peptide is compared to the SRM/MRM signature chromatographic peak area of the internal standard peptide, and this numerical comparison indicates either the absolute molarity and/or absolute weight of the native peptide present in the original protein preparation from the biological sample. Quantitative data for fragment peptides are displayed according to the amount of protein analyzed per sample.

In order to develop the SRM/MRM assay for the Her2 fragment peptide additional information beyond simply the peptide sequence is utilized by the mass spectrometer. That additional information permits the mass spectrometer, (e.g., a triple quadrupole mass spectrometer) to perform the correct and focused analysis of the specified Her2 fragment peptide. An important consideration when conducting an SRM/MRM assay is that such an assay may be effectively performed on a triple quadrupole mass spectrometer. That type of a mass spectrometer presently may be considered to be the most suitable instrument for analyzing a single isolated target peptide within a very complex protein lysate that may consist of hundreds of thousands to millions of individual peptides from all the proteins contained within a cell. The additional information provides the triple quadrupole mass spectrometer with the correct directives to allow analysis of a single isolated target peptide within a very complex protein lysate that may consist of hundreds of thousands to millions of individual peptides from all the proteins contained within a cell.

Although SRM/MRM assays can be developed and performed on any type of mass spectrometer, including a MALDI, ion trap, or triple quadrupole, presently the most advantageous instrument platform for SRM/MRM assay is often considered to be a triple quadrupole instrument platform. The additional information about target peptides in general, and in particular about the specified Her2 fragment peptide, may include one or more of the mono isotopic mass of each peptide, its precursor charge state, the precursor m/z value, the m/z transition ions, and the ion type of each transition ion. The peptide sequence of this specified Her2 fragment peptide and the necessary additional information as described for this specified Her2 fragment peptide is shown in Table 1.

TABLE 1

| SEQ ID | Peptide sequence | Mono Isotopic Mass | Precursor Charge State | Precursor m/z | Transition m/z | Ion Type |
|---|---|---|---|---|---|---|
| SEQ ID NO: 1 | ELVSEFSR | 967.066 | 2 | 483.748 | 538.261 | y4 |
| | | | 2 | 483.748 | 625.294 | y5 |
| | | | 2 | 483.748 | 724.362 | y6 |

To determine an appropriate reference level for Her2 quantitation, tumor samples are obtained from a cohort of patients suffering from a cancer, for example, gastric cancer. The tumor samples are formalin-fixed using standard methods and the level of Her2 in the samples is measured using the methods as described above. The tissue samples may also be examined by IHC and FISH using methods that are well known in the art. The patients in the cohort are treated with an anti-Her2 therapeutic agent, such as trastuzumab, in combination with standard chemotherapy, such as paclitaxel, and the response of the patients is measured using methods that are well known in the art, for example by recording the overall survival of the patients at time intervals after treatment. A suitable reference level can be determined using statistical methods that are well known in the art, for example by determining the lowest p value of a log rank test.

Once a reference level has been determined it can be used to identify those patients whose Her2 expression level is high enough that they are likely to benefit from including an anti-Her2 therapeutic agent in their treatment regimen, together with those patients whose Her2 expression level is sufficiently low that use of an anti-Her2 agent is unlikely to be of therapeutic benefit. The skilled artisan will recognize that anti-Her2 agents are used as part of a regimen that utilizes additional drugs or combinations of drugs. Treatment regimens for treating cancer with non-targeted standard chemotherapy are known in the art and drugs that are used can include fluorouracil, Cyramza (Ramucirumab), Docetaxel, Doxorubicin Hydrochloride, Herceptin (Trastuzumab), and Mitomycin C. Drug combinations used in gastric cancer include FU-LV (fluorouracil plus leucovorin), TPF (Docetaxel, cisplatin and fluorouracil) and XELIRI (Capecitabine plus Irinotecan Hydrochloride). One or more of these drugs can be used individually and in combination with strikingly similar outcomes with no one single agent historically showing better response over another. Thus this entire group of agents are not targeted to a specific oncoprotein(s) and thus are considered standard chemotherapy and are very much interchangeable with respect to treatment and outcome. However, historically it has been shown that treatment of a gastric cancer patient, and cancer patients in general, with one or more of these standard chemotherapy agents does in fact demonstrate a striking improvement in Progression Free Survival (PFS) and Overall Survival (OS) when compared to not treating the patient standard chemotherapy.

Levels of Her2 as determined by SRM in patient samples typically are expressed in amol/µg, although other units can be used. The skilled artisan will recognize that a reference level can be expressed as a range around a central value, for example, +/−250, 150, 100, 50 or 25 amol/µg. In the specific example described in detail below a suitable reference level was found to be 1825 amol/µg but the skilled artisan will recognize that levels higher or lower than this can be selected based on clinical results and experience. It has been found that for many cancers, such as gynecological, esophageal, gallbladder, pancreatic, breast, lung, and gastric cancers, that a level of about 2000 amol/µg or greater, (optionally 2000+/−250, 150, 100, 50 or 25 amol/µg) is predictive of response to trastuzumab-containing treatment regimens. Experimental Data Demonstrating Development of a Predictive Value of HER2 Protein Expression Levels for Trastuzumab Sensitivity in a HER2 Positive Gastric Cancer Population.

Patients

A total of 249 patients from Seoul National University Hospital were identified with histologically confirmed recurrent or metastatic gastric cancer. Formalin-fixed, paraffin-embedded (FFPE) biopsies were collected prior to treatment and Her2 was analyzed by immunohistochemistry (IHC) and/or FISH. A total of 153 patients determined to be Her2+ by either IHC and/or FISH were used for this study. A total of 95 patients treated with a combination of trastuzumab and standard chemotherapy (Cohort 1) were analyzed and used for survival analysis, while a control population of 58 patients treated with only standard chemotherapy (Cohort 2) were analyzed and used for survival analysis.

Methods

FFPE tumor tissue from all 153 patients in this study was microdissected to collect tumor cells and solubilized for downstream mass spectrometry analysis using the Liquid Tissue reagents as described above. Her2 protein levels were quantitated using mass spectrometry by the selected reaction monitoring method (SRM) across all patients. Progression-free survival (PFS) and overall survival (OS) for these patient populations as a function of Her2 protein levels were estimated by the Kaplan-Meier method. Cox regression models that included an interaction term between Her2 protein levels and treatment groups (trastuzumab with chemotherapy or chemotherapy alone) were fit to evaluate the effect of Her2 on the comparison. The optimal cutoff of Her2 SRM to predict trastuzumab sensitivity was determined by the lowest p value of log rank test.

Results

Histological characteristics of the 95 patients of cohort 1 treated with the combination trastuzumab+standard chemotherapy are shown in Table 2.

TABLE 2

| | | HER2+ Tmab+ N = 95 |
|---|---|---|
| Age | median years (range) | 64 (22-85) |
| Sex | Male | 78 (82.1) |
| | Female | 17 (17.9) |
| ECOG | 0 | 19 (20.0) |
| | 1 | 66 (69.5) |
| | 2 | 10 (10.5) |
| Palliative setting | Metastatic | 64 (67.4) |
| | Recurrent | 31 (32.6) |
| Tumor location | Stomach | 89 (93.7) |
| | GEJ | 6 (6.3) |
| HER2 status | Positive | 95 (100) |
| | Negative | 0 |
| Pathology | Adenocarcinoma | 90 (94.7) |
| | PCC | 2 (2.1) |
| | Others | 3 (3.2) |
| Signet ring cell component† | No | 86 (90.5) |
| | Yes | 9 (9.5) |
| Lauren classification | Intestinal | 22 (23.2) |
| | Diffuse | 5 (5.3) |
| | Mixed | 4 (4.2) |
| | Unknown | 64 (67.4) |
| Overall survival | median months (95% CI) | 22.5 (17.5-31.9) |
| PFS of Tmab | median months (95% CI) | 9 (7.0-11.2) |
| Follow-up duration | median months (range) | 39.1 (7.1-110.2) |

Data presented as N (%) unless otherwise specified.
Abbreviations:
Tmab, trastuzumab;
ECOG, Eastern Cooperative Oncology Group;
GEJ, gastroesophageal junction;
PCC, poorly cohesive carcinoma;
OS, overall survival;
HR, hazard ratio.
†Contains signet ring feature: either pure signet ring cell carcinoma (i.e. poorly cohesive carcinoma) or adenocarcinoma containing signet ring features.

Her2 levels for each individual patient tumor were determined and the resulting Kaplan-Meier curves demonstrate a striking benefit to treatment with trastuzumab+chemotherapy in patients whose Her2 levels were higher than the cutoff of 1825 amol/ug (>1825 amol/ug) as determined by the lowest p value of log rank test. As shown in FIG. 1, comparison between cohort 1 patients >1825 amol/ug and cohort 1 patients <1825 amol/ug demonstrate significant differences in PFS whereby cohort 1>1825 amol/ug have PFS=10.6 months vs. cohort 1<1825 amol/ug have PFS=7 months. Statistical analysis indicates p value=0.0200 making this a statistically significant finding.

FIG. 1 also shows that cohort 1>1825 amol/ug realizes even greater significant benefit from treatment with trastuzumab+chemotherapy when compared to cohort 2 which received only standard chemotherapy. Patients in cohort 1>1825 amol/ug show PFS=10.6 months whereas patients in cohort 2 show PFS=6 months. Statistical analysis indicates p value=0.0020 making this a highly statistically significant finding.

FIG. 1 also shows the comparison between cohort 1 patients <1825 amol/ug (trastuzumab+chemotherapy) and cohort 2 patients (chemotherapy alone). The comparison shows very similar PFS whereby cohort 2 patients <1825 amol/ug demonstrated PFS=7 months and cohort 1 patients demonstrated PFS=6 months. Statistical analysis by the log rank test indicates p value=0.500 for this comparison demonstrating no significant benefit from treating Her2+ patients with the anti-Her2 agent trastuzumab over standard chemotherapy alone where patient Her2 values <1825 amol/ug.

Figure 2:
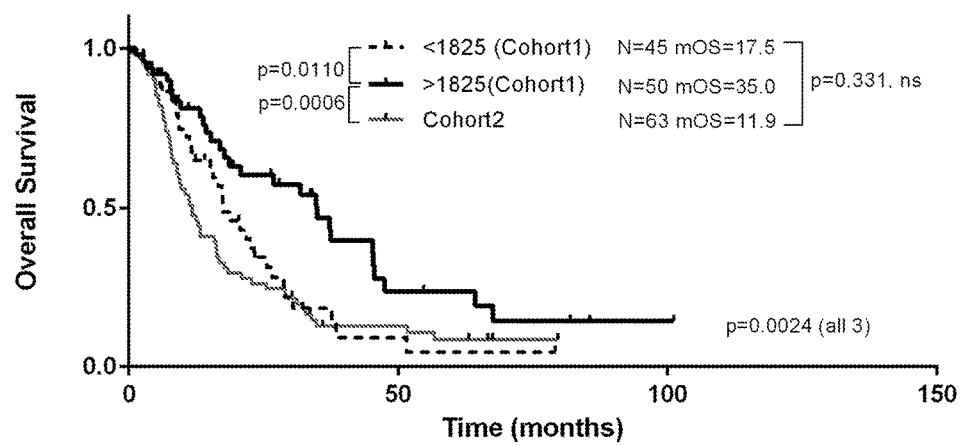
FIG. 2 shows a comparison of overall survival of patients treated with trastuzumab plus chemotherapy versus treatment with chemotherapy alone. The data compare patients with Her2>1825 amol/µg and those with Her2<1825 amol/µg.

Similar results showing benefits to trastuzumab treatment in patients from cohort 1>1825 amol/ug are realized in Overall Survival (OS) under the same statistical methods. Kaplan-Meier curves demonstrate a striking benefit to treatment in OS with trastuzumab+chemotherapy in patients whose Her2 levels are higher than the cutoff of 1825 amol/ug (>1825 amol/ug) as determined by the lowest p value of log rank test. As shown in FIG. 2, comparison between cohort 1 patients >1825 amol/ug and cohort 1 patients <1825 amol/ug demonstrates significant differences in PFS whereby cohort 1>1825 amol/ug have OS=35 months vs. cohort 1<1825 amol/ug have PFS=17.5 months. Statistical analysis indicates p value=0.0110, making this a statistically significant finding.

FIG. 2 further shows that cohort 1>1825 amol/ug realized even greater significant benefit from treatment with trastuzumab+chemotherapy when compared to cohort 2 which received only standard chemotherapy. Patients in cohort 1>1825 amol/ug showed OS=35 months whereas patients in cohort 2 showed OS=11.9 months. Statistical analysis indicates p value=0.0006 making this a highly statistically significant finding.

FIG. 2 also shows the comparison between cohort 1 patients <1825 amol/ug (trastuzumab+chemotherapy) and cohort 2 patients (chemotherapy alone). The comparison showed similar OS whereby cohort 1 patients <1825 amol/ug demonstrated OS=17.5 months and cohort 2 patients demonstrated PFS=11.9 months. Statistical analysis by the log rank test indicated p value=0.331 for this comparison demonstrating no significant benefit from treating Her2+ patients showing Her2 values <1825 amol/ug with the anti-Her2 agent trastuzumab+chemotherapy over chemotherapy alone.

amount of an anti-Her2 therapeutic agent when the level of the Her2 fragment peptide is below said reference level.

2. The method of claim 1 wherein said reference level is 1825 amol/µg, +/−150 amol/µg of biological sample protein analyzed.

3. The method of claim 1 wherein said reference level is 1825 amol/µg, +/−100 amol/µg of biological sample protein analyzed.

4. The method of claim 1 wherein said reference level is 1825 amol/µg, +/−50 amol/µg of biological sample protein analyzed.

5. The method of claim 1 wherein said reference level is 1825 amol/µg, +/−25 amol/µg of biological sample protein analyzed.

6. The method of claim 1, wherein said protein digest comprises a protease digest.

7. The method of claim 6, wherein said protease digest comprises a trypsin digest.

8. The method of claim 7, wherein the mode of mass spectrometry used is Selected Reaction Monitoring (SRM), Multiple Reaction Monitoring (MRM), and/or multiple Selected Reaction Monitoring (mSRM).

9. The method of claim 1, wherein the specified Her2 peptide has the amino acid sequence as set forth as SEQ ID NO:1.

10. The method of claim 1, wherein the tumor sample is a cell, collection of cells, or a solid tissue.

11. The method of claim 10, wherein the tumor sample is formalin fixed solid tissue.

12. The method of claim 11, wherein the tissue is paraffin embedded tissue.

The invention claimed is:

1. A method of treating a patient suffering from gastric cancer comprising:
   (a) quantifying the level of a specified Her2 fragment peptide in a protein digest prepared from a tumor sample obtained from the patient and calculating the level of the Her2 peptide in said sample by selected reaction monitoring using mass spectrometry;
   (b) comparing the level of said Her2 fragment peptide to a reference level, wherein said reference level is about 1825 amol/µg+/−250 amol/µg, and
   (c) treating the patient with a therapeutic regimen comprising standard chemotherapy and an effective amount of an anti-Her2 therapeutic agent when the level of the Her2 fragment peptide is higher than said reference level or
   (d) treating the patient with a therapeutic standard chemotherapy regimen that does not comprise an effective 13. The method of claim 1, wherein quantifying the specified Her2 fragment peptide comprises determining the amount of the Her2 peptide in said sample by comparing to a spiked internal standard peptide of known amount, wherein both the native peptide in the biological sample and the internal standard peptide corresponds to the same amino acid sequence of the Her2 fragment peptide as shown in SEQ ID NO:1.

14. The method of claim 4, wherein the internal standard peptide is an isotopically labeled peptide, wherein the isotopically labeled internal standard peptide comprises one or more heavy stable isotopes selected from $^{18}O$, $^{17}O$, $^{15}N$, $^{13}C$, $^{2}H$ or combinations thereof.

15. The method of claim 1, wherein detecting and quantitating the specified Her2 fragment peptide can be combined with detecting and quantitating other peptides from other proteins in multiplex so that the treatment decision about which agent used for treatment is based upon specific levels of the specified Her2 fragment peptide in combination with other peptides/proteins in the biological sample.

16. The method of claim 1 wherein when said level of said specified peptide is higher than said reference level, then said anti-Her2 therapeutic agent comprises trastuzumab.

* * * * *